United States Patent [19]

Dougherty et al.

[11] 4,212,637
[45] Jul. 15, 1980

[54] ORTHODONTIC FACE BOW

[76] Inventors: Harry L. Dougherty, 14434 Hamlin St., Van Nuys, Calif. 91401; William W. Beazley, 5400 Balboa Blvd., Encino, both of Calif. 91316

[21] Appl. No.: 651,686

[22] Filed: Jan. 23, 1976

[51] Int. Cl.² .............................................. A61C 3/00
[52] U.S. Cl. ...................................................... 433/5
[58] Field of Search ................................. 32/14 D, 14

[56] References Cited

U.S. PATENT DOCUMENTS

| | | | |
|---|---|---|---|
| 664,412 | 12/1900 | Knapp | 32/14 D |
| 2,141,190 | 12/1938 | Linde | 32/14 A |
| 3,866,322 | 2/1975 | Broussard et al. | 32/14 D |
| 3,903,604 | 9/1975 | Snead | 32/14 D |
| 3,997,971 | 12/1976 | Moss | 32/14 D |
| 4,087,915 | 5/1978 | Andrews | 32/14 D |
| 4,115,921 | 9/1978 | Armstrong | 32/14 D |

*Primary Examiner*—Robert Peshock
*Attorney, Agent, or Firm*—Marvin Jabin

[57] ABSTRACT

An orthodontic face bow for use in the correction of malposed teeth, especially for children. The face bow includes an externally applied outer bow and an internally applied inner bow which extends into the wearer's mouth and which separates from the outer bow when the latter is pulled.

8 Claims, 7 Drawing Figures

ORTHODONTIC FACE BOW

BACKGROUND OF THE INVENTION

Extra-oral anchorage and traction have been of invaluable aid in the treatment of dental malocclusions, and were first reported as being used in the treatment of maxillary protrusions in the 1880's. Changes wherein the extra-oral forces have aided in remodeling the maxillae and maxillary dentition have been amply demonstrated.

One of the most commonly used appliances has been the so-called Kloehn face bow, named after its originator, S.J. Kloehn. The Kloehn face bow and variations thereof, such as those shown in U.S. Pats. Nos. 721,655, 3,036,380, 3,111,758, 3,137,841, 3,311,978, 3,314,151 and 3,429,044, all utilize an inner bow which is either welded or otherwise affixed to an outer bow in a manner such that the two bows cannot be readily separated when the outer bow is pulled As a result thereof, there have been a number of serious injuries reported, as where someone, such as a playmate, has playfully grabbed the outer bow and pulled it forward to such an extent that the free ends of the inner bow were completely removed from the mouth. Then, under the tension from the elastic in the high-pull headgear, the outer bow slipped out of the playmate's grasp and the pointed ends of the inner bow were driven into both of the patient's eyes, resulting in total blindness.

SUMMARY OF THE INVENTION

According to the preferred embodiment of the present invention, an orthodontic face bow includes an externally applied outer bow and an internally applied inner bow which separates from the outer bow when the latter is pulled. The extremities of the inner bow are coupled to the patient's teeth by means for preventing the unintentional release therefrom, and the inner and outer bows are coupled by separable means which normally permits the outer bow to apply force to the inner bow, but which enables the outer bow to separate easily from the inner bow when the outer bow is pulled away from the inner bow, thereby avoiding serious injury to the patient, especially to the patient's eyes.

In addition, the face bow system has interchangeable parts which are compatible with dental and oral hygiene and in which patient cooperation can be maximized with a minimum of instruction or help.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings, in which:

DESCRIPTION OF THE PREFERRED EMBODIMENT

Figure 1:
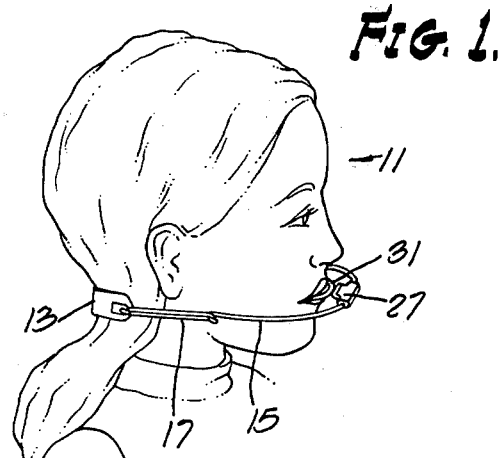
FIG. 1 shows a patient wearing an orthodontic face bow according to the present invention.

Turning now to the drawings, FIG. 1 shows patient 11 with neck band 13 around the back of her neck. Neck band 13 is connected to outer bow 15 by means of elastic or rubber band 17. Other forms of headgear could be used just as well as neck band 13 in order to apply force to outer bow 15 via rubber band 17.

Figure 3:
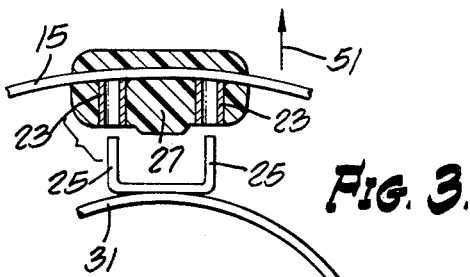
FIG. 3 is a plan view of a portion of the orthodontic face bow shown in FIG. 2, showing the inner and outer bows separated.
Figure 2:
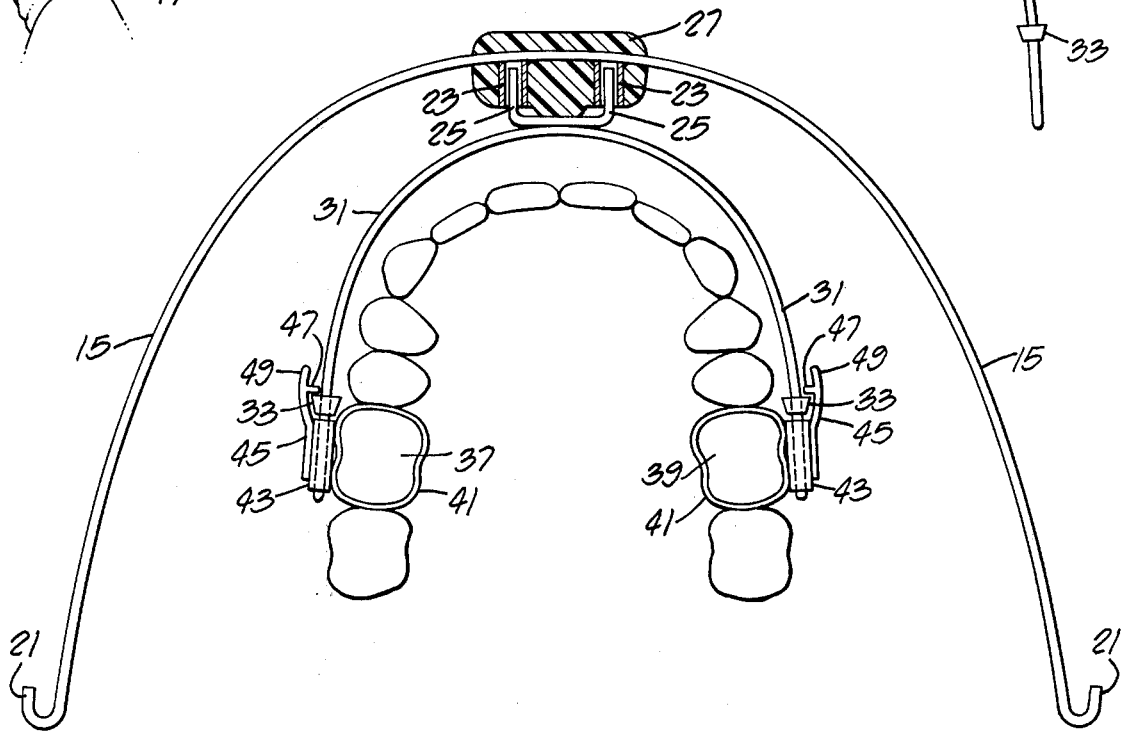
FIG. 2 is a plan view of the orthodontic face bow shown in FIG. 1.

FIGS. 2 and 3 show outer bow 15 having a hook 21 at each end and a pair of tubular sleeves 23 for receiving the tubular pins 25. Sleeves 23 are encased in epoxy material 27 for strength. Pins 25 are welded or soldered to inner bow 31, which has a cone-shaped tube stop 33 mounted near the extremity of each of the ends thereof.

Teeth 35 are shown, with left molar 37 and right molar 39 each having a molar band 41 around it. Each molar band 41 is welded or soldered to a molar tube 43, each of which is, in turn, welded or soldered to a spring 45. Each spring 45 has a shoulder 47 and a finger grip 49. When each of the ends of inner bow 31 is inserted in a molar tube 43 until tube stop 33 abuts against molar tube 43, the shoulder 47 prevents the withdrawal of inner bow 31 from the molar tubes 43 until the springs 45 are bent by the application of force to finger grips 49.

FIG. 3 shows how inner and outer bows 31 and 15, respectively, are separated when force is applied to outer bow 15 in the direction indicated by arrow 51. The pull exerted upon outer bow 15 merely results in the withdrawal of pins 25 from sleeves 23. The shoulders 47 exert sufficient restraining force upon tube stops 33 to prevent the withdrawal of the ends of inner bow 31 from within molar tubes 43 unless finger grips 49 are utilized to bend springs 45 sufficiently to permit tube stops 33 to clear shoulders 47.

Figure 4:
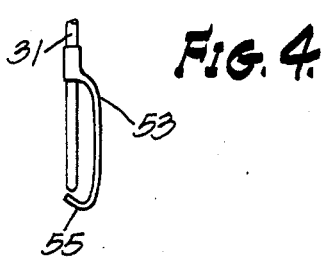
FIG. 4 is a plan view of a different embodiment of the present invention.
Figure 5:
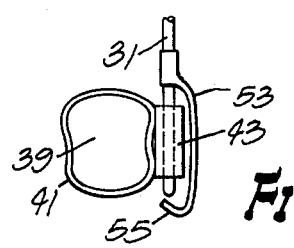
FIG. 5 is a plan view showing the embodiment of FIG. 4 in operation.

FIGS. 4 and 5 shows a different embodiment in which a tube stop clip 53 is used instead of the tube stops 33. When the extremity of inner bow 31 is inserted within molar tube 43, the end 55 of tube stop clip 53 prevents the withdrawal of inner bow 31 from molar tube 43 until end 55 is deflected out of the way. The end 55 is curved or rounded, so that it will automatically be deflected out of the way by molar tube 43 and permit the extremity of inner bow 31 to be inserted within the tube 43.

Figure 6:
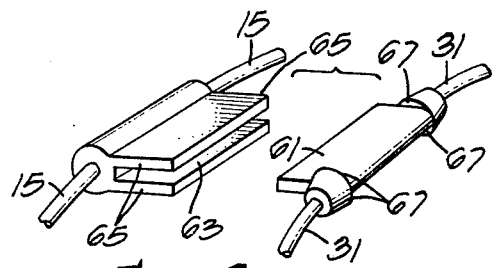
FIG. 6 is a perspective view of a third embodiment of the present invention.

FIG. 6 shows a different embodiment in which the pins 25 and sleeves 23 of FIG. 2 are replaced by a tongue 61 and a groove 63. Tongue 61, which is welded or soldered to inner bow 31, can be inserted within groove 63, which is welded or soldered to outer box 15, so that the edges 65 will abut against shoulder stops 67.

Figure 7:
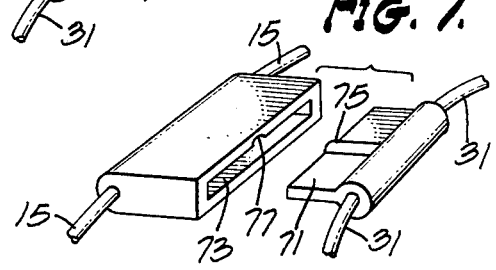
FIG. 7 is a perspective view of a fourth embodiment of the present invention.

FIG. 7 shows another embodiment in which the pins 25 and sleeves 23 of FIG. 2 are replaced by a key 71 and a boxed slot 73. Key 71, which is welded or soldered to inner bow 31, can be inserted within slot 73, which is welded or soldered to outer bow 15.

Extension 75 is provided on the key 71 and a corresponding groove 77 is provided in the slot 73, in order to prevent inverted insertion of key 71 within slot 73, so that the coupling of the inner and outer bows can occur in only one way. This is important when the face bows have an up-side and a down-side, depending upon the desired force vector. In addition, sometimes one leg of the outer bow is made longer or shorter than the other leg, making it important that the outer and inner bows fit together the same way each time the patient puts on the face bow.

In the case of the key and slot embodiment shown in FIG. 7, as well as the tongue and groove embodiment shown in FIG. 6 and the pin and tube embodiment shown in FIG. 2, the inner bow will separate from the outer bow when the latter is pulled away from the patient's mouth. As a result thereof, serious injury to the patient will be avoided. In addition, the inner and outer bows can be interchanged with other inner and outer bows, respectively, resulting in interchangeable parts which are compatible with dental and oral hygiene. Patient cooperation is thereby greatly enhanced.

While particular embodiments of the present invention have been shown and described, it will be obvious to those skilled in the art that changes and modifications may be made without departing from this invention in its broader aspects, and that the intention is to cover all such changes and modifications as fall within the true spirit and scope of this invention.

We claim:

1. An orthodontic face bow comprising:
   (a) inner bow means,
   (b) outer bow means, and
   (c) coupling means having first means rigidly connected to said outer bow means and second means rigidly connected to said inner bow means, said first and second means being separably interconnected, said first and second means nonpivotally securely abutting against each other when force is applied to the ends of said outer bow means in a first direction, and readily disconnecting when force is applied to said outer bow means in a second direction.

2. Apparatus according to claim 1 in which said first direction is generally toward the wearer of said apparatus, and said second direction is generally away from the wearer of said apparatus.

3. Apparatus according to claim 1 in which said inner bow means has at least two extremities, each of which is connected to stop means which cooperates with a band around one of the wearer's teeth to securely fasten said extremities to the teeth of the wearer of said apparatus, each of said bands being connected to tube means and each of said extremities being insertable within one of said tube means until said stop means abut against said tube means, and including retaining means which prevents the withdrawal of said extremities from said tube means when said stop means abuts against said tube means, unless said retaining means is manually released.

4. Apparatus according to claim 3 in which said coupling means includes a pin and sleeve combination.

5. Apparatus according to claim 3 in which said coupling means includes a tongue and groove combination.

6. Apparatus according to claim 3 in which said coupling means includes a key and slot combination, said key having an extension and said slot having a corresponding groove which cooperates with said extension, thereby preventing inverted insertion of said key within said slot.

7. Apparatus according to claim 3 in which said retaining means includes spring means having shoulder means for retaining said stop means until said spring means is deflected.

8. Apparatus according to claim 3 in which said retaining means includes an elongated end on said stop means which locks onto said tube means until said elongated end is deflected, said stop means being a cylindrial tube which is rigidly connected to said inner bow means and integral with said elongated end.

* * * * *